United States Patent [19]

Munn et al.

[11] Patent Number: 5,747,046
[45] Date of Patent: May 5, 1998

[54] **VACCINE CONTAINING A PROTEIN COMPLEX FORM *HAEMONCHUS CONTORTUS***

[76] Inventors: Edward Albert Munn, 72 Station Road, Fulbourn, Cambridge CB1 5ES, England; Trevor Stanley Smith, 6 The Close, Babraham, Cambridge CB2 4AQ, England

[21] Appl. No.: 347,198

[22] Filed: Nov. 21, 1994

Related U.S. Application Data

[60] Continuation of Ser. No. 20,526, Feb. 22, 1993, abandoned, which is a division of Ser. No. 761,749, filed as PCT/GB90/00416, Mar. 19, 1990, published as WO90/11086, Oct. 4, 1990, abandoned.

Foreign Application Priority Data

Mar. 17, 1989 [GB] United Kingdom .................. 8906156

[51] Int. Cl.$^6$ .................. A61K 39/00; C07K 14/00
[52] U.S. Cl. .................. 424/265.1; 531/350; 531/403
[58] Field of Search .................. 424/265.1; 530/350, 530/403

[56] References Cited

FOREIGN PATENT DOCUMENTS

| 8800835 | 2/1988 | WIPO . |
| 8900163 | 1/1989 | WIPO . |

OTHER PUBLICATIONS

Behnke et al, Parisitology Today 3(7): 200–206, 1987.
Hotez et al, Parisitology Today 3(8): 247–249, 1987.
Tavernor et al, Paristology Immunology 14: 645–655, 1992.
Harlow et al "Antibodies a Laboratory Manual", Cold Spring Harbor Labs, NY, 1988, p. 513.
Munn et al, Parasitology 94:385–397, 1987.

*Primary Examiner*—James C. Housel
*Assistant Examiner*—Julie Krsek-Staples
*Attorney, Agent, or Firm*—Nikaido, Marmelstein, Murray & Oram LLP

[57] ABSTRACT

A protein complex H45 is described whose components are glycoproteins isolable from the intestinal microvillus plasma membrane of a parasitic nematode, such as *Haemonchus contortus*. This complex includes protein H4.5, which has an apparent molecular weight on sodium dodecyl sulphate polyacrylamide gel electrophoresis (SDS-PAGE) of about 45 Kd under reducing conditions and about 90 Kd under non-reducing conditions, as well as proteins H4.9 and H5.3 which have apparent molecular weights on SDS-PAGE of about 49 Kd and about 53 Kd respectively both under reducing and under non reducing conditions. Protein complex H45 and its components can be used, optionally together with the already known protein doublet H110D, to form a vaccine which can reduce the weight of worms in sheep infected with *Haemonchus contortus* by an average of 91% and the parasite egg production by an average of 94.5%.

6 Claims, 4 Drawing Sheets

FIG. 1 SCHEMATIC FLOWCHART FOR THE PREPARATION OF PROTEIN DOUBLET H110D AND PROTEIN COMPLEX H45

VACCINE CONTAINING A PROTEIN COMPLEX FORM *HAEMONCHUS CONTORTUS*

This Application is a continuation of application Ser. No. 08/020,526, filed Feb. 22, 1993, now abandoned, which is a division of application Ser. No. 07/761,749, filed as PCT/GB90/00416, Mar. 19, 1990, published as WO90/11086, Oct. 4, 1990, now abandoned.

This invention relates to production of materials for use as anthelmintic agents and as protective immunogens, and to the use of such materials.

The blood-feeding nematode Haemonchus infects the lining of the gastro-intestinal tract of ruminants. World-wide it is of very considerable economic importance having effects which range from reduction in weight gain, loss of production and agalactia through to death of domesticated animals. A related nematode Ostertagia has similar effects. The diseases haemonchosis and ostertagiasis are characterised by wasting due in part to anorexia associated with severe infections. In sheep and cattle Ostertagia is the most important in winter rainfall areas, while Haemonchus is more important in summer rainfall zones. In Australia, for example it is estimated that approximately one third of the 300 million sheep in the country are likely to be infected with Haemonchus. Two other genera, Trichostrongylus and Nematodirus, are of particular economic importance. Trichostronagylus is one of the most important causes of parasitic gastro-enteritis in warmer regions. Nematodirus, especially *N. battus*, can cause acute, often fatal, enteritis in lambs.

Related blood-ingesting nematodes, the hookworms, infect ruminants, dogs, cats, other carnivores, and humans. Over 700 million humans are infected with hookworms, especially *Necator americanus*, with 700–900,000 new cases per year and 50–60,000 deaths due to the ravages of these parasites. Ancylostoma and the related hookworm Uncinaria are considered the most pathogenic helminths of the small intestine of the dog and cat. Species of another hookworm, Bunostomum, infect ruminants and *B. phlebotomum* which infects cattle is of particular commercial importance in North America. Species of Ancylostoma also infect humans. It has been shown (E. A. Munn and C. A. Greenwood, *Parasitology* (1983) 87, 129–137 and *Philosophical Transactions of the Royal Society* B, 306, 1–18, 1984) that Haemonchus and the hookworm Ancylostoma caninum have many important similarities in the structure of the sub-cellular components at the luminal surface of their intestines. Thus, as well as being an economically important parasite of ruminants, Haemonchus potentially provides a useful model for the development of vaccines against hookworms.

Extracts containing the protein doublet H110D obtained from Haemonchus give protection against haemonchosis when injected into sheep. This doublet, B110D, is found at the luminal surface of the intestine of Haemonchus. The preparation and use of H110D have been described in WO-A-88/00835. However, although the methods described in WO-A-88/00835 suffice to characterise the protein doublet H110D, they do not readily admit to being scaled up to permit facile production of the protein doublet H110D in experimentally and commercially useful quantities.

In WO-A-89/00163 a protein with a molecular weight on sodium dodecyl sulphate polyacrylamide gel electrophoresis (SDS-PAGE) of 41 Kd is described in larvae of the parasitic nematode *Trichostrongylus colubriformis*. This protein was extracted from homogenised third stage larvae of *T. colub-riformis*. The gene for this protein has been cloned. A very similar DNA sequence was demonstrated in *Haemonchus contortus* although expression of the Haemonchus gene in vivo was not reported. This document also reports results of vaccination trials in sheep against *Haemonchus contortus* with an antigen expressed by recombinant organisms. In these trials reduced egg counts were reported in the faeces, with an average overall of 40% reduced egg counts. At slaughter 63 days after vaccination the vaccinated group of sheep were found to contain, on average 52% fewer worms than the control group.

There is a need to provide a convenient procedure for isolating in non-denatured form the protein doublet H110D, and its components, from solutions containing same, such as homogenates of *Haemonchus contortus* or other parasitic nematode, or solutions containing such proteins expressed from suitably genetically modified prokaryotic or eukaryotic organisms, including transgenic animals or cells. There is also a need to provide further immunogens effective against parasitic nematodes.

The present invention accordingly seeks to provide a novel and improved process for the production of the protein doublet H110D and its component proteins, as well as of protein fragments derived therefrom. It further seeks to provide a novel protective immunogen for potential use against nematodes and its production.

According to one aspect of the present invention there is provided a protein, polypeptide or peptide comprising one or more of the sequences of amino acid residues (a) to (o) or homologues thereof:

(a) M G Y P V V K V E E F (SEQ ID NO:1)

(b) M G F P V L T V E S (SEQ ID NO:2)

(c) M E/F N F L I E/V T/E A G (SEQ ID NO:3)

(d) M K P/E T/V L D/A T/K L - I T (SEQ ID NO:4)

(e) M L A L D Y H S - F V (SEQ ID NO:5)

(f) M L A E/Y D Q/A E D V (SEQ ID NO:6)

(g) M G F P L V T V E A F Y (SEQ ID NO:7)

(h) M K T P E F A V/L Q A F/T A T S/G F P (SEQ ID NO:8)

(i) K H/Y N/V S P A A E N/L L N/G (SEQ ID NO:9)

(j) K - T S V A E A F N (SEQ ID NO:10)

(k) K A A E V A E A F D - I - - - K G (SEQ ID NO:11)

(l) K A V E V/P A E A F D D I T?Y - - G P S (SEQ ID NO:12)

(m) K - E Q T E I F N M (SEQ ID NO:13)

(n) K - - - P F N/D I E A L (SEQ ID NO:14)

(o) D Q A F S T D A K. (SEQ ID NO:15)

In the above sequences (a) to (o) the single letter amino acid code is used wherein the letters mean: A, alanine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; and Y, tyrosine. Also uncertainties are shown either by the form P/E, where the upper letter represents the most likely correct amino acid based on the strength of the signal, or by a question mark; a sign "-" means an unknown residue.

Preferred proteins, polypeptides or peptides are of the general formula x-y-z, wherein x and z each represent independently of each other a hydrogen atom or a residue of an amino acid, of a protected amino acid, of a peptide, or of a polypeptide, and y represents one of the sequences (a) to (o) set out above. Such proteins, polypeptides or peptides may be glycosylated or non-glycosylated. At least one of x and z may comprise at least one of the sequences (a) to (o) set out above which may be the same as or different from y.

The invention further provides DNA coding for such a protein, polypeptide or peptide, as well as a polynucleotide sequence coding for such a protein, polypeptide or peptide.

It also relates to a method of recovering the protein doublet H110D, components thereof, or polypeptide fragments thereof from a feed solution containing same which includes the step of contacting the feed solution with immobilised antibodies to H110D, followed by selective elution of the bound H110D, components or fragments thereof. Preferably the feed solution has previously been contacted with an immobilised lectin.

The human hookworm *Necator americanus* may be cultured in a laboratory animal host. We have found that the sub-cellular structure of the intestine of adult Necator closely resembles that of Ancylostoma and that extracts from Necator containing integral membrane proteins closely match in their behaviour on sodium dodecyl sulphate-polyacrylamide gel electrophoresis (SDS-PAGE) the pattern of proteins obtained from Haemonchus by the same extraction procedures. Notably the extracts contain a protein doublet with a relative molecular weight of 110,000 daltons corresponding to H110D from Haemonchus and also a group of protein bands with relative molecular weights (in reduced form) of about 53,000, about 49,000 and about 45,000 daltons corresponding to a group of other intestinal microvillar membrane proteins from Haemonchus. This latter group of proteins is herein called protein complex H45. Initially we identified the protein component of this complex having a relative molecular weight ($M_r$) of about 45,000 daltons which we designated as protein H4.5. The other proteins of protein complex H45 having relative molecular weights (in reduced form) of about 53,000 and about 49,000 daltons can be designated as H5.3 and H4.9 respectively.

Extracts containing both the protein doublet H110D and protein complex H45 obtained from Haemonchus give protection against haemonchosis when injected into sheep. In our vaccination trials we have observed better than 98% reduction in parasite egg output and better than 92% reduction in worm burden with a vaccine containing H110D. A vaccine based on protein complex H45 also provided protection against *Haemonchus contortus* in sheep; in this case vaccinated sheep showed on average a reduction of 38% in female worm count and a reduction of 68% in egg production compared with a control group of animals. H4.5, H4.9 and H5.3 are also found at the luminal surface of the intestine of Haemonchus.

Protein complex H45 exhibits three protein bands with relative molecular weights (in reduced form) on SDS-PAGE of about 53,000, about 49,000 and about 45,000 daltons respectively. The components of this group co-purify and have an epitope in common which binds to the same monoclonal antibody. The bands with $M_r$ of about 53,000 daltons (protein H5.3) and about 45,000(protein H4.5) stain more intensely with protein stains and are broader than the band with $M_r$ of about 49,000 daltons. When run on SDS-PAGE at low concentration the proteins making up the three bands of protein complex H45 may each be resolved further into two bands which run very close together (i.e. they are doublets).

The invention further provides the proteins H4.5, H4.9 and H5.3, as well as mixtures of two or more thereof. In particular it provides the protein complex H45 in partially purified or fully purified form, that is to say in a form in which it behaves essentially as a coherent component upon electrophoresis under non-denaturing conditions or in a suitable chromatographic technique. It also relates to the use of the protein complex H45 and its components as protective immunogens against Haemonchus and other parasitic nematodes alone or in admixture with the protein doublet H110D or one of the components of the H110D doublet. Hence the invention further provides vaccines containing any or all of the components of the protein complex H45 alone or in admixture with one or more immunogens which induce immunity to one or more parasitic nematodes, such as the protein doublet H110D or one of the component proteins of that doublet.

It is also contemplated that, as it is to be expected that the digestive tracts of the blood ingesting stages of other helminths such as the lung worm Dictyocaulus, the heartworm Dirofilaria, and the trematodes Fasciola, Dicrocoelium, and Schistosoma also contain surface membrane glycoproteins analogous to or homologous with H110D and protein complex H45, vaccines based on H110D and/or H45 or analogues or homologues thereof can perhaps be used against one or more of such helminths.

The feed solution used in the method of the invention for recovering the protein doublet H110D may be a homogenate containing H110D produced by homogenisation of *Haemonchus contortus*, its intestine or membrane derived therefrom, or another suitable parasitic nematode, or a broth or serum containing H110D, a component thereof or a fragment thereof, expressed by a suitably genetically engineered prokaryotic or eukaryotic organism or cell. Alternatively the feed solution used in the process of the invention may be a partially purified extract obtained, for example, from such a homogenate, broth or serum. For such partial purification advantage may be taken of the experimental observation that, although H110D is soluble in Triton X-100 and in similar non-ionic detergents, such as Thesit (polyoxyethylene 9-lauryl ether), as well as in zwitterionic detergents, such as CHAPS, (3-[3-cholamidopropyl]-dimethylammonio]-1-propanesulphonate), it is not soluble in the nonionic detergent Tween 20 (polyoxyethylenesorbitan monolaurate) although other membrane associated proteins are soluble in this detergent. (The word "Triton" is a registered trade mark and the word "Tween" is a trade mark). This differential solubility in detergents allows the removal of some detergent-soluble but unwanted proteins prior to selection of the glycoproteins of interest by affinity chromatography according to the process of the invention.

In one preferred process according to the invention advantage is taken of the further experimental observation that the proteins of the doublet H110D each have carbohydrate groups attached thereto. The presence of these carbohydrate groups enables the proteins of the H110D doublet, as well as fragments thereof which still carry the carbohydrate groups, to be separated in the process of the invention by affinity chromatography using one of the class of proteins known as lectins as complementary binding substance (or ligand) immobilised on an insoluble supporting matrix.

The proteins H4.5, H4.9 and H5.3, which together make up the protein complex H45, are integral membrane glycoproteins present in the microvilli of the intestine of *Haemonchus contortus*. They interact with the lectin Concanavalin A and do not bind to the strong anion exchange resin MonoQ (highly cross linked beaded agarose with attached charged groups) (Pharmacia), in 20 mM-TrisHCl, pH 7.2, 0.1% Thesit. (The word "MonoQ" is a registered trade mark). H110D binds to MonoQ under these conditions. H4.5 has an apparent molecular weight ($M_r$) of approximately 45,000 daltons on SDS-PAGE when run under reducing conditions and an $M_r$ of about 90,000 daltons when run under non-reducing conditions. However, the other components of the protein complex H45, i.e. proteins H5.3 and H4.9, have apparent molecular weights ($M_r$) of about 53,000 and about 49,000 daltons respectively on SDS-PAGE when run both under reducing conditions and under non-reducing conditions. H4.5 and the other proteins of the H45 complex have one or more epitopes in common with non-denatured H110D.

The invention further relates to a method of separating the immunogen protein complex H45 from a solution containing same which comprises contacting the solution with an immobilised protein reagent selected from lectins, antibodies to H110D and antibodies to the protein complex H45, followed by selective elution of the bound components, to form an eluate containing the protein complex H45, adsorption of the protein complex H45 from the eluate on an anion exchange resin, and subsequent elution therefrom. The solution containing the protein complex H45 can be obtained by extraction of *Haemonchus contortus*, from another parasitic nematode, such as *Necator americanus*, or from a genetically engineered organism or cell culture.

The invention further relates to immunogens containing one or more of the following amino acid sequences:

(p) M G Y P V V K V E E F - A T A L (SEQ ID NO:16)

(q) M G F P V L T V E S - Y?- T (SEQ ID NO:17)

(r) M E/F N F L I E/V T/E A G - I T (SEQ ID NO:18)

(s) M G F P L V T V E A F Y - T S (SEQ ID NO:19)

(t) M K T P E F A V/L Q A F/T A T S/G F P (SEQ ID NO:8)

(u) M K P/E T/V L D/A T/K L - I T - G (SEQ ID NO:20)

(v) M L A L D Y H S - F V G? (SEQ ID NO:21)

(w) M L A E/Y D Q/A E D V (SEQ ID NO:7)

(x) K H/Y N/V S P A A E N/L L N/G (SEQ ID NO:9)

(y) K - T S V A E A F N (SEQ ID NO:10)

(z) K A A E V A E A F D - I - - - K G (SEQ ID NO:11)

(aa) K A V E V/P A E A F D D I T?Y - - G P S (SEQ ID NO:12)

(bb) K - E Q T E I F N M (SEQ ID NO:13)

(cc) K - - - P F N/D I E A L (SEQ ID NO:14)

(dd) D Q A F S T D A K (SEQ ID NO:15)

(Uncertainties are shown either by the form P/E, where the upper letter represents the most likely correct amino acid based on the strength of the signal, or by a question mark. The sign "-" means that no identifiable residue was obtained for that position.)

The invention further relates to oligonucleotides based on any one of the amino acid residue sequences (a) to (o) or (p) to (dd) set out above, for example one having the sequence 5'ATG GCA TTC CCG TTG GTC ACA GTC GAA GCC TTC TAC3' (SEQ ID NO:22), which bind to genomic DNA and CDNA obtained from *Haemonchus contortus*.

The invention further provides immunogens which when injected into a mammalian host induce immunity to haemonchosis and which contain epitopes recognised by monoclonal antibodies specific for the protein doublet H110D and the protein complex H45 prepared from Haemonchus.

According to yet another aspect of the invention there is provided a vaccine containing the protein complex H45 or a protein component thereof, possibly in any combination with H110D or with other immunogens, which induces immunity to one or more parasitic nematodes.

The invention thus provides a purified protein complex (H45) derived from a parasitic nematode comprising first, second and third protein components having apparent molecular weights on sodium dodecyl sulphate polyacrylamide gel electrophoresis (SDS-PAGE) of about 53,000 daltons, about 49,000 daltons, and about 45,000 daltons respectively under reducing conditions and about 53,000 daltons, about 49,000 daltons, and about 90,000 daltons respectively under non reducing conditions. Such a purified protein complex can be derived from a species of Haemonchus, Necator, Ancylostoma, Uncinaria, Oesophagostomum, Dictyocaulus, Strongylus, Dirofilaria, Bunostomum, Ostertagia, Trichostrongylus, or Nematodirus, for example from *Haemonchus contortus*. There is also contemplated a protein which is an analogue, homologue, derivative, fragment or component of the protein complex H45.

Preferred proteins according to the invention include:

(a) a purified protein designated herein H4.5 isolable from the intestinal microvillus plasma membrane of a parasitic nematode, said purified protein having an apparent molecular weight on sodium dodecyl sulphate polyacrylamide gel electrophoresis of about 45,000 daltons under reducing conditions and of about 90,000 daltons under non-reducing conditions;

(b) a purified protein designated herein H4.9 isolable from the intestinal microvillus plasma membrane of a parasitic nematode having an apparent molecular weight on sodium dodecyl sulphate polyacrylamide gel electrophoresis both under reducing and non-reducing conditions of about 49,000 daltons; and (c) a purified protein designated herein H5.3 isolable from the intestinal microvillus plasma membrane of a parasitic nematode having an apparent molecular weight on sodium dodecyl sulphate polyacrylamide gel electrophoresis both under reducing and non-reducing conditions of about 53,000 daltons.

The parasitic nematode from which such proteins are derived may be a species of Haemonchus, Necator, Ancylostoma, Uncinaria, Oesophagostomum, Dictyocaulus, Strongylus, Dirofilaria, Bunostomum, Ostertagia, Trichostrongylus, or Nematodirus, for example *Haemonchus contortus*.

Also provided in accordance with the invention is a vaccine for inducing protection in a living mammal against a parasitic nematode or suitable trematode which comprises an effective amount of a protein, polypeptide or peptide according to the invention, as well as a vaccine for inducing protection in a living mammal against a parasitic nematode or suitable trematode which comprises an effective amount of the protein complex H45 or a component protein thereof. Such a vaccine may further contain an amount of the protein doublet H110D, of one of the components thereof, or of an analogue, homologue, derivative or fragment of at least one component thereof. It may further contain an amount of the protein contortin, or of an analogue, homologue, derivative or fragment thereof. Typically the vaccine will contain an amount per unit dosage of the protein complex H45, optionally admixed with protein doublet H110D, or an analogue, homologue or derivative thereof, ranging from about 0.1 to about 25 µg per kg of live weight of the mammal to be protected. Hence in the case of a lamb weighing typically 25 kg, the amount per unit dosage will range from about 0.25 µg up to about 625 µg, whereas with an adult human being typically weighing 70 kg the amount per unit dosage may range from about 7 µg up to about 1750 µg. Preferably the amount per unit dosage will correspond to between about 1 µg and about 20 µg, even more preferably between about 2 µg and about 15 µg, per kilogram of body weight.

Such vaccines can be used to induce protection in a living mammal against a parasitic nematode by injection of a unit dosage containing an effective amount of the relevant protective antigen or antigens.

Also within the scope of the invention is a prokaryotic organism, eukaryotic organism, or cell genetically modified to express at least one component of the protein complex H45 or an analogue, homologue, derivative or fragment thereof, or one which has been genetically modified to express at least one protein, polypeptide or peptide comprising one or more of the sequence of amino acids (a) to (o) or (p) to (dd) set out above.

In yet another of its aspects the invention provides a process for the in vitro production of antibodies in which antibodies are raised against a protein complex H45 or H110D or a protein component thereof.

Also useful are proteins, polypeptides and peptides which are specifically recognised by circulating antibodies induced in a vertebrate by injection of the protein complex H45 or H110D or of a protein component thereof.

In the accompanying drawings:

BRIEF DESCRIPTION OF THE DRAWINGS

In FIG. 2 lanes a and b contain proteins and peptides of known $M_r$ which are shown in kD. Lane c contains the peptides obtained by CNBr cleavage of H110D. The numbered bands were taken for amino acid sequence analysis, the results of which are set out in Table 1 below.

In FIG. 4 lanes (a) and (b) show proteins of known molecular weight, lane (c) purification to stage 1 of FIG. 1, lane (d) the protein complex H45-enriched fraction obtained from anion exchange chromatography, lane (e) purification to stage 3 of FIG. 1, and lane (f) electrophoretically purified H110D.

Figure 1:
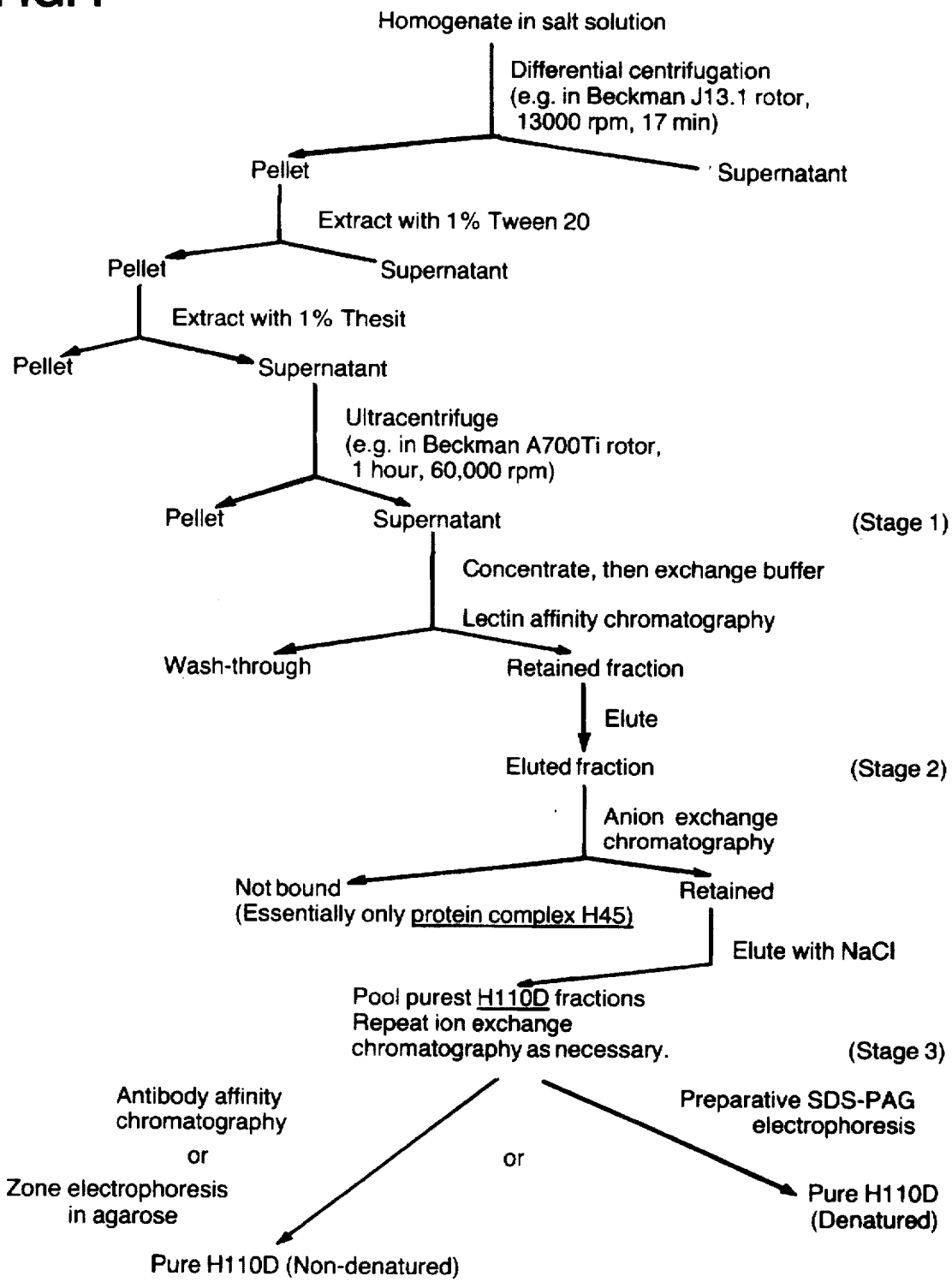
FIG. 1 is a schematic flowchart for the preparation of protein doublet H110D and complex protein H45.

In an alternative preferred process monoclonal antibodies specific for the protein doublet H110D and for other proteins present in the fraction containing H110D eluted from a lectin affinity column have been produced by two procedures. In one procedure conventional methodology was followed: mice were injected with detergent extracts of Haemonchus purified to stage 2 as shown in the accompanying schematic FIG. 1, or with extracts purified to stage 3 (FIG. 1) or with the protein complex H45-enriched fraction. When the antibody titre in serum samples measured by ELISA using samples of the injected proteins as antigen was judged sufficiently high the mice were killed and spleen cells obtained. These were fused with mouse myeloma cell lines NSO and 653 cells. Fused cells producing antibodies to components of Haemonchus were selected and cloned. Antibodies produced by these clones when cultured were collected and their specificity determined by the technique of Western blotting in which antigens separated by SDS-PAGE are electrophoretically transferred to nitro-cellulose and there can be probed by the antibodies. In the second procedure sheep were injected with detergent extracts of Haemonchus purified to stage 1 (FIG. 1). When the specific antibody titres in serum samples were sufficiently high, blood samples were taken and lymphocytes isolated therefrom; the sheep were killed and popliteal lymph nodes excised and lymphocytes obtained from them. The lymphocytes were fused with mouse myeloma cell line NSO to form sheep-mouse heterohybridomas. Heterohybridomas expressing sheep antibodies specific for the Haemonchus proteins were selected and cloned and the antibodies they produced were collected. Such monoclonal antibodies which react specifically with protein H110D, with protein complex H4.5 and its component proteins, e.g. protein H4.5, and with other proteins which occur in detergent extracts of Haemonchus (and with antigens in Ostertagia) can alternatively be used singly or consecutively as ligand in purification of H110D, its components and fragments thereof, and protein complex H45 in the affinity chromatography step of the process of the present invention.

The invention is further illustrated in the following Examples.

EXAMPLE 1

(The stages are numbered as depicted in FIG. 1.)

Fresh or freeze-thawed *Haemonchus contortus* were chopped finely and homogenised in approximately 6 volumes of phosphate-buffered saline (PBS, 10 mM sodium phosphate, 0.9% NaCl, pH 7.2). The resulting homogenate was then centrifuged at about 20,000 g for 17 minutes. The supernatant liquor was removed and the pellet rehomogenised in about 4 volumes PBS. Following recentrifugation the supernatant was removed, the pellet resuspended in about 5 volumes of PES containing 1% Tween 20 and then left for 1 hour on ice with occasional mixing by inversion. The extract was centrifuged for 17 minutes at about 20,000 g and the supernatant liquor discarded. The pellet was extracted in this way once again with 1% Tween in PBS and then extracted three times with 1% Thesit detergent (Boehringer Mannheim) in PBS over a period of up to 16 hours. The supernatant liquors obtained by centrifuging each extract for 17 minutes at about 20,000 g from the three extractions were combined and centrifuged for about $11 \times 10_6$ g. min. The resultant supernatant liquor was retained (stage 1, FIG. 1). It was concentrated and the buffer exchanged for 5 mM acetate buffer pH 5.2, containing 1 mM calcium chloride, 1 mM manganese chloride, 0.1% Thesit and 0.02% sodium azide (Con A buffer). This solution was then subjected to affinity chromatography using the lectin Concanavalin A (Con A) bound to affi-gel (cross-linked agarose beads, Bio-gel A-5 m agarose gel) (Bio-Rad). (The word "affi-gel" is a registered trade mark). The protein doublet H110D bound to the column, as did the protein complex H45. Unbound proteins were eluted with Con A buffer. The H110D and protein complex H45 were then eluted with 0.5M methyl-D-glucopyranoside in Con A buffer (stage 2, FIG. 1). This material was then concentrated and transferred to 20 mM TrisHCl containing 0.1% Thesit, pH 7.2 and applied to a MonoQ (Pharmacia) ion exchange chromatography column. The protein complex H45 did not bind. The protein H110D was eluted with a 0-25% gradient of the application buffer containing 1M M-NaCl. Fractions containing H110D were pooled and rechromatographed on the ion exchange column (stage 3).

EXAMPLE 2

When the procedure of Example 1 is repeated but with the ligand Concanavalin A replaced in the affinity chromatography step with lentil lectin or with wheat germ agglutinin, both of which specifically bind to the carbohydrate portion of H110D and of H45, similar results are obtained.

EXAMPLE 3

The procedure of Example 1 was repeated except that the ligand consisted of monoclonal (or polyclonal) antibodies specific for H110D. In this procedure components of unpurified or partially purified H110D were adsorbed to a column or membrane to which antibodies specific for H110D or other Haemonchus protein had been bound. Proteins which were not bound by the antibodies were washed out and the bound protein was eluted using either changed pH, high salt concentrations, a chaotropic agent or a combination of these. The ligands may be bound to any suitable matrix; CNBr-activated Sepharose (beaded agarose reacted with CNBr) or CH-Sepharose (beaded agarose with 6-carbon spacer arms) (Pharmacia), Affi-Prep (polymeric matrix beads with attached activated groups) (Bio-Rad Laboratories), Zetaffinity (membrane composite of cellulose and synthetic polymers) disk or cartridge (CUNO Inc. Life Sciences Division) or Immobilon affinity membrane (polyvinylidene difluonide mebrane) (Millipore Corporation) are suitable matrices. (The words "Sepharose", "Affi-Prep", "Zetaffinity" and "Immobilon" are trade marks).

The antibodies were produced by the procedures described above.

Binding of the antibodies to the matrix was achieved by activation of the reactive groups as appropriate.

EXAMPLE 4

The procedure of Example 1 was repeated except that an ion-exchange chromatography step using ZetaPrep QAE disks (CUNO Inc. Life Sciences Division) was introduced after stage 1. (The word "ZetaPrep" is a trade mark). The supernatant liquor from stage 1 was concentrated and transferred to 20 mM TrisHCl-pH 7.2 containing 0.1% Thesit and passed through a ZetaPrep QAE disk. The H110D enriched fraction was eluted with application buffer containing a step gradient of 0.05M, 0.1M, 0.2M and 0.25M NaCl. The buffer was then exchanged for ConA buffer.

EXAMPLE 5

The procedure of Example 4 was followed except that after the extractions with the solution of Tween 20 the pellet was washed with 20 mM-TrisHCl and then extracted three times with 1% Thesit in 20 mM trisHCl, pH 7.2.

EXAMPLE 6

The procedure of Example 1 was followed except that extraction with the solutions of Tween 20 and Thesit were omitted and instead extraction was made with 1.8% Triton X-114. After the ultracentrifugation step the supernatant liquor was brought to 30° C. to effect phase separation. After centrifugation at low speed at above 20° C. the detergent phase was diluted with 1% Thesit in Con A buffer at ambient temperature. The homogeneous solution thus obtained was then subjected to affinity and ion exchange chromatography as set out in Example 1. This method solubilises little of the H45 protein complex group.

EXAMPLE 7

The efficacy of the protein H110D purified to stage 3 (FIG. 1) by the method of Example 1 from extracts by differential extraction with detergent solutions, affinity chromatography using Con A and ion-exchange chromatography in a vaccine against haemonchosis has been demonstrated. Five of six Clun Forest sheep were protected by injection with H110D purified by the procedure described above and used at about 15 µg/kg live weight. The average weight of worms recovered from the five animals 35 days after challenge infection with 10,000 infective third stage larvae was reduced by 98.6% compared to the controls. The egg production by the parasites was reduced by 99.1% compared to the controls. The sixth animal was partially protected; its worm burden was reduced by only 53% and the parasite egg production was reduced by 72.3% compared to the average of the controls. Considering all six animals injected with the purified H110D there was an average 91% reduction in total worm weight and 94.5% reduction in parasite egg production compared to the control group which were treated identically except that the injections they received did not contain Haemonchus protein.

Antisera from the protected sheep bind strongly to H110D and to the proteins of protein complex H45, such as protein H4.5, on Western blots of extracts purified to stage 1 (FIG. 1). This indicates that H4.5 and mixtures thereof with one or more of H5.3 and H4.9 may be particularly good immunogens, since judged from Coomassie blue staining of H110D purified to stage 3 only about 1% of the material injected (i.e. about 0.15 µg/kg live weight) consisted of protein complex H45, some 98% of the total injected being H110D. Alternatively it indicates that H110D and at least one of the components of protein complex H45 have epitopes in common. These alternatives are not mutually exclusive. Cross-reaction to both H110D and protein complex H45 by sheep and by mouse monoclonal antibodies on Western blots and by ELISA has been demonstrated.

Figure 3:
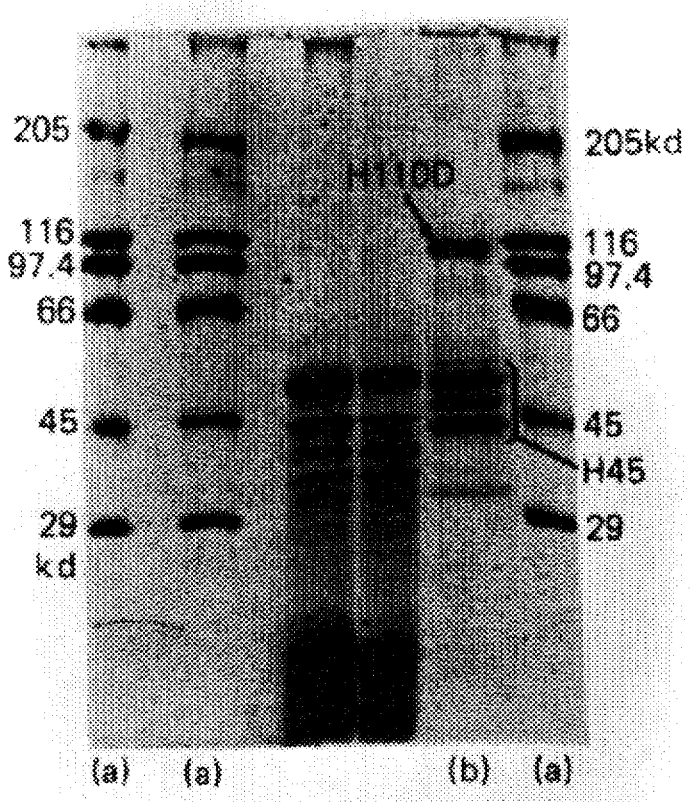
FIG. 3 shows the results obtained by Coomassie blue stained SDS-PAGE separation of (a) standard proteins of known molecular weight and (b) membrane proteins extracted by the detergent Thesit from the microvilli of the intestine of *Haemonchus contortus*, the sample having been reduced with 2-mercaptoethanol and run under reducing conditions.
Figure 4:
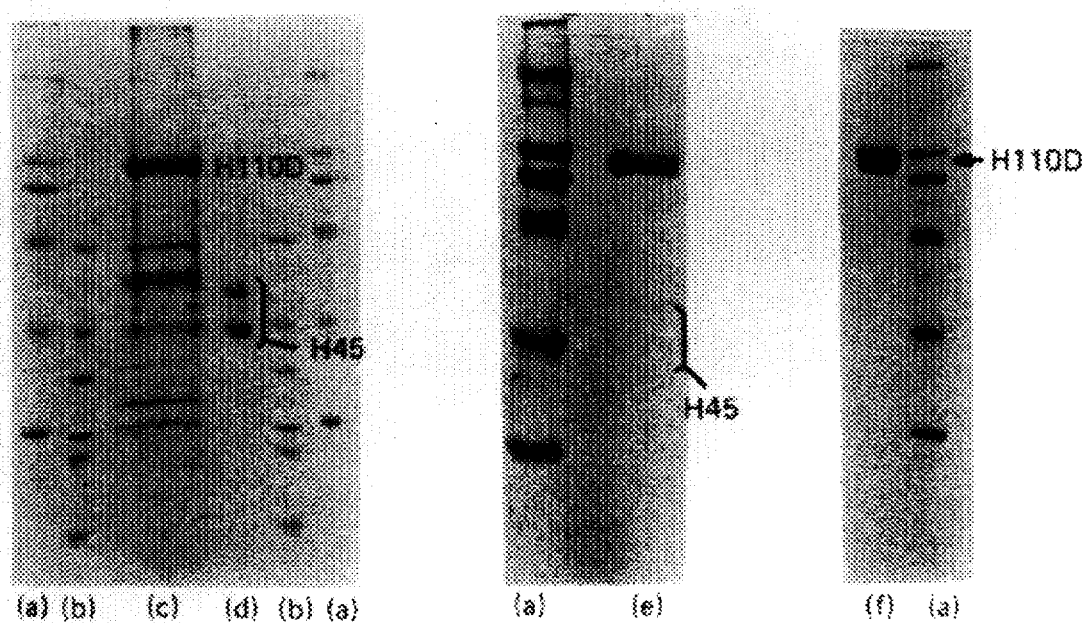
FIG. 4 includes SDS-PAGE patterns of fractions at various stages in the purification procedure summarised in FIG. 1.

Protein H4.5 and the other proteins of the protein complex H45 are present, with H110D, in the microvillar membrane of the intestine of Haemonchus (see FIG. 3). Thesit extracts of the intestines of Ancylostoma, Uncinaria, and Necator run on SDS-PAGE under reducing conditions also have a band with a $M_r$ of 45,000 daltons as well as bands corresponding to the proteins of the protein complex H45 having $M_r$s of about 49,000 and about 53,000 daltons respectively. When run on SDS-PAGE under non-reducing conditions H4.5 has a $M_r$ of about 90,000 daltons, whereas H5.3 and H4.9 still have $M_r$s of about 53,000 and 49,000 daltons respectively and there is no band with an $M_r$ of about 45,000 daltons.

The protein doublet H110D may be further purified in a non-denatured form by electrophoresis in 1% agarose in barbitone buffer pH 8.4 containing 1% Thesit or other non-ionic detergent. The protein should be transferred back to a buffer at pH 7.2 as soon as it is eluted from the gel. Alternatively the protein doublet H110D is further purified by antibody affinity chromatography in which antibodies specific for proteins other than H110D are used to remove these proteins, or antibodies specific for H110D are used to select the protein doublet.

In the same way using the appropriate immobilised antibodies the protein complex H45 may be further purified.

Figure 2:
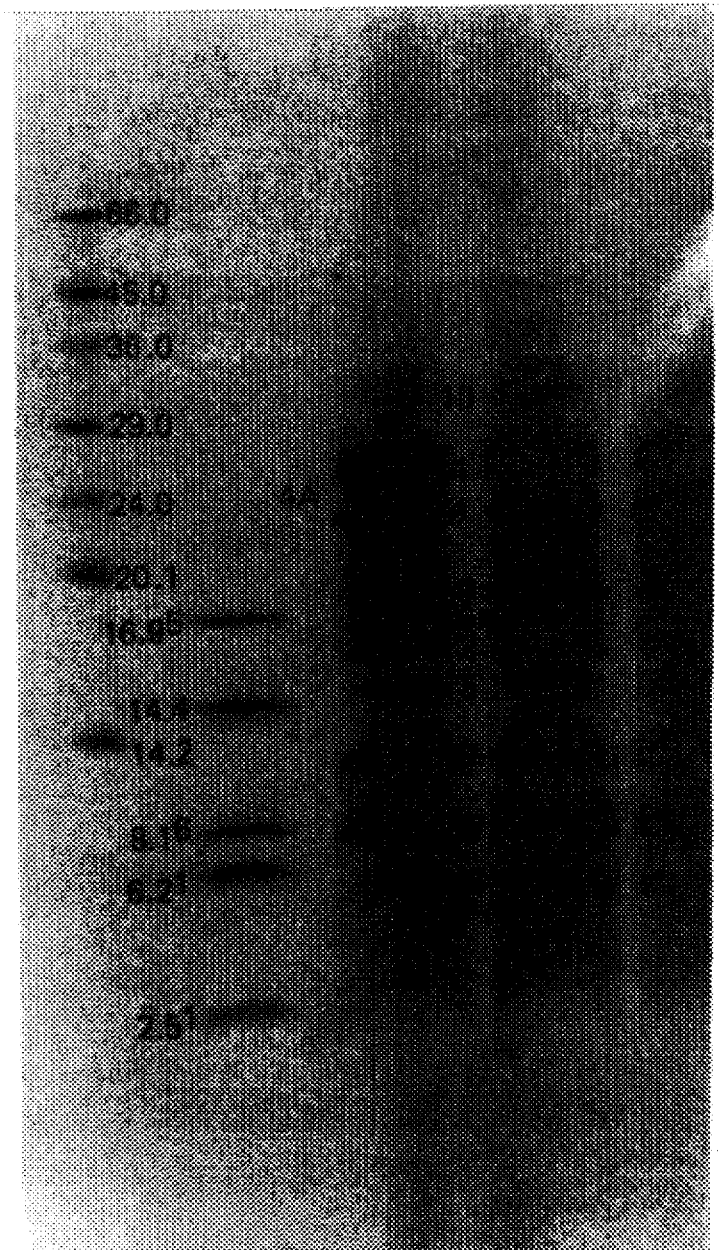
FIG. 2 shows the results obtained by Coomassie blue staining on SDS-PAGE of peptides obtained by cleavage of H110D with CNBr.

The protein doublet H110D may be purified in a denatured form by SDS-PAGE and electrophoretic elution. Pure H110D prepared in this way is not suitable for vaccination but is suitable for chemical characterisation including fragmentation with proteolytic enzymes and chemical cleavage reagents such as CNBr. FIG. 2 shows the characteristic pattern of fragments obtained by SDS-PAGE of the products of the cleavage of H110D with molar excess of CNBr in 70% formic acid, in the dark, under $N_2$ at room temperature for 4 hours. Digestion under the same conditions for 18 hours gives essentially the same pattern.

The N-terminal sequences obtained by Edman degradation of the CNBr fragments electrophoretically transferred to nitrocellulose, lightly stained with Coomassie blue, excised and analysed in a gas-phase amino acid sequenator are presented in part (a) in the following Table 1.

Using these reagents, band 10 (FIG. 2) is probably highly glycosylated since it binds large amounts of Concanavalin A but stains only lightly with the protein stain Coomassie blue. Bands 1, 2, 3, 4 and 7 are probably less highly glycosylated than band 10. They bind Concanavalin A in approximate proportion to their degree of staining with Coomassie blue. Band 7 is the only peptide obtained by CNBr cleavage to

TABLE 1

Partial amino acid sequence data of peptides obtained by (a) CNBr cleavage, (b) Lys—C digestion, and (c) trypsin digestion of protein doublet H110D

| | Peptide No. | Approx $M_r$ | Sequence |
|---|---|---|---|
| (a) | 1 | 23 Kd | M G Y P V V K V E E F - A T A L (SEQ ID NO: 16) |
| | 2 | 16 Kd | M G F P V L T V E S - Y? - T (SEQ ID NO: 17) |
| | 3 | 8 Kd | M E/F N F L I E/V T/E A G - I T (SEQ ID NO: 18) |
| | 4 | 25.5Kd | M G F P L V T V E A F Y - T S (SEQ ID NO: 19) |
| | 4A | 27 Kd | M K T P E F A V/L Q A F/T A T S/G F P (SEQ ID NO: 8) |
| | 5 | 15 Kd | M K P/E/V T L D/A/K T L - I T - G (SEQ ID NO: 20) |
| | 6 | 17.5Kd | M L A L D Y H S - F V G? (SEQ ID NO: 21) |
| | 9 | 18 Kd | M L A E/Y D Q/A E D V (SEQ ID NO: 7) |
| (b) | 1.7 | 24? Kd | K H/Y/V N S P A A E N/L L N G (SEQ ID NO: 9) |
| | 2.3 | 42 Kd | K - T S V A E A F N (SEQ ID NO: 10) |
| | 3.4 | 47 Kd | K A A E V A E A F D - I - - - K G (SEQ ID NO: 11) |
| | 3.6 | 40 Kd | K A V E V/P A E A F D D I T? Y - - G P S (SEQ ID NO: 12) |
| | 2.2 | 43 Kd | K - E Q T E I F N M (SEQ ID NO: 13) |
| | 2.7 | 18 Kd | K - - - P F N/D I E A L (SEQ ID NO: 14) |
| (c) | 12 | - | D Q A F S T D A K (SEQ ID NO: 15) |

Notes to Table 1.
1. The single letter amino acid code is A, alanine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; and Y, tyrosine.
2. Uncertainties are shown either by the form P/E, where the upper letter represents the most likely correct amino acid based on the strength of the signal, or by a question mark. A sign "-" means that no identifiable residue was obtained for that position.
3. The other bands analysed (see FIG. 2) either gave no useful signal or mixtures of equal strength.

Western blots of the CNBr digests may be probed with monoclonal and polyclonal antibodies and with lectins.

which the mouse monoclonal antibodies designated TSS 1/9.7 and TSS 1/9.16 bind.

Three peptides, designated MUN2, MUN3 and MUN4, respectively, having the sequences

M G Y P V V K V E E F, (SEQ ID NO:1)

M G F P V L T V E S, (SEQ ID NO2)

and

M G F P L V T V E A F Y (SEQ ID NO:7)

respectively corresponding to the N-terminal sequences of CNBr fragments 1, 2 and 4 respectively were synthesised by conventional methods and were injected into rabbits and sheep. Specific antibodies resulted. The antibodies bound to denatured H110D purified by electrophoresis in PAG (polyacrylamide gel) and the antibodies to MUN4 also bound to purified non-denatured H110D. Antibodies to MUN4 may be used in affinity chromatography for purification of non-denatured H110D. These peptides (MUN2, MUN3 and MUN4) are not protective epitopes as such but they may form part of protective epitopes. Further, the other peptide sequences may form in whole or in part the protective epitopes.

We claim:

1. A protein complex purified from the intestinal microvillus plasma membrane of *Haemonchus contortus* and designated herein H45, wherein said protein complex is substantially free from H110D, exhibits cross-reactivity to antibodies against H110D, and comprises glycosylated proteins.

2. A purified protein complex designated H45 which is derived from the intestinal microvillus plasma membrane of *Haemonchus contortus*, said protein complex comprising first, second and third glycosylated protein components having apparent molecular weights on sodium dodecyl sulphate polyacrylamide gel electrophoresis (SDS-page) of about 53,000 daltons, about 49,000 daltons and about 45,000 daltons respectively under reducing conditions, and about 53,000 daltons, about 49,000 daltons and about 90,000 daltons respectively under non-reducing conditions, and wherein said protein complex is substantially free of H110D.

3. A purified protein complex according to claim 2, in which said parasitic nematode is *Haemonchus contortus* and wherein said first, second and third glycosylated protein components possess cross-reactivity to antibodies against H110D.

4. A vaccine effective for protecting a living mammal against *Haemonchus contortus* comprising an effective amount of a protein complex according to claim 2, wherein said protein is purified from the intestinal microvillus plasma membrane of *Haemonchus contortus*.

5. A vaccine according to claim 4, further comprising an effective amount of the protein contortin.

6. A method of protecting a living mammal against *Haemonchus contortus* comprising injecting said mammal with an amount of a vaccine according to claim 4 effective to protect against said *Haemonchus contortus*.

\* \* \* \* \*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Met Gly Tyr Pro Val Val Lys Val Glu Glu Phe
    1                    5                      10

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

Met Gly Phe Pro Val Leu Thr Val Glu Ser
    1                    5                      10

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

Met Xaa Asn Phe Leu Ile Xaa Xaa Ala Gly
    1                    5                      10

( 2 ) INFORMATION FOR SEQ ID NO:4:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

Met Lys Xaa Xaa Leu Xaa Xaa Leu Xaa Ile Thr
    1                    5                      10

( 2 ) INFORMATION FOR SEQ ID NO:5:

( i ) SEQUENCE CHARACTERISTICS:

( A ) LENGTH: 11 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:5:

Met Leu Ala Leu Asp Tyr His Ser Xaa Phe Val
1               5                   10

( 2 ) INFORMATION FOR SEQ ID NO:6:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:6:

Met Leu Ala Xaa Asp Xaa Glu Asp Val
1               5

( 2 ) INFORMATION FOR SEQ ID NO:7:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:7:

Met Gly Phe Pro Leu Val Thr Val Glu Ala Phe Tyr
1               5                   10

( 2 ) INFORMATION FOR SEQ ID NO:8:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:8:

Met Lys Thr Pro Glu Phe Ala Xaa Gln Ala Xaa Ala Thr Xaa Phe
1               5                   10                  15

Pro ( 2 ) INFORMATION FOR SEQ ID NO:9:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:9:

Lys Xaa Xaa Ser Pro Ala Ala Glu Xaa Leu Xaa
1               5                   10

( 2 ) INFORMATION FOR SEQ ID NO:10:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:10:

```
Lys  Xaa  Thr  Ser  Val  Ala  Glu  Ala  Phe  Asn
1              5                        10
```

( 2 ) INFORMATION FOR SEQ ID NO:11:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:11:

```
Lys  Ala  Ala  Glu  Val  Ala  Glu  Ala  Phe  Asp  Xaa  Ile  Xaa  Xaa  Xaa
1              5                        10                        15

Lys  Gly
```

( 2 ) INFORMATION FOR SEQ ID NO:12:

( i ) SEQUENCE CHARACTERISTICS:
    ( A ) LENGTH: 19 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:12:

```
Lys  Ala  Val  Glu  Xaa  Ala  Glu  Ala  Phe  Asp  Asp  Ile  Xaa  Tyr  Xaa
1              5                        10                        15

Xaa  Gly  Pro  Ser
```

( 2 ) INFORMATION FOR SEQ ID NO:13:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:13:

```
Lys  Xaa  Glu  Gln  Thr  Glu  Ile  Phe  Asn  Met
1              5                        10
```

( 2 ) INFORMATION FOR SEQ ID NO:14:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:14:

```
Lys  Xaa  Xaa  Xaa  Pro  Phe  Xaa  Ile  Glu  Ala  Leu
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
Asp Gln Ala Phe Ser Thr Asp Ala Lys
1               5
```

(2) INFORMATION FOR SEQ ID NO:16:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Met Gly Tyr Pro Val Val Lys Val Glu Glu Phe Xaa Ala Thr Ala
1               5                   10                  15
Leu
```

(2) INFORMATION FOR SEQ ID NO:17:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Met Gly Phe Pro Val Leu Thr Val Glu Ser Xaa Xaa Xaa Thr
1               5                   10
```

(2) INFORMATION FOR SEQ ID NO:18:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Met Xaa Asn Phe Leu Ile Xaa Xaa Ala Gly Xaa Ile Thr
1               5                   10
```

(2) INFORMATION FOR SEQ ID NO:19:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Met Gly Phe Pro Leu Val Thr Val Glu Ala Phe Tyr Xaa Thr Ser
 1               5                   10              15
```

( 2 ) INFORMATION FOR SEQ ID NO:20:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

```
Met Lys Xaa Xaa Leu Xaa Xaa Leu Xaa Ile Thr Xaa Gly
 1               5                   10
```

( 2 ) INFORMATION FOR SEQ ID NO:21:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Met Leu Ala Leu Asp Tyr His Ser Xaa Phe Val Xaa
 1               5                   10
```

( 2 ) INFORMATION FOR SEQ ID NO:22:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

```
ATGGCATTCC CGTTGGTCAC AGTCGAAGCC TTCTAC                                  36
```